US010004400B2

(12) United States Patent
Nakamoto et al.

(10) Patent No.: US 10,004,400 B2
(45) Date of Patent: Jun. 26, 2018

(54) PROBE AND OPTICAL IMAGING APPARATUS FOR DIAGNOSIS

(75) Inventors: Ryou Nakamoto, Kanagawa (JP); Yoshiteru Yamaguchi, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days. days.

(21) Appl. No.: 13/616,663

(22) Filed: Sep. 14, 2012

(65) Prior Publication Data
US 2013/0012810 A1 Jan. 10, 2013

(30) Foreign Application Priority Data

Mar. 19, 2010 (JP) ................................ 2010-064873

(51) Int. Cl.
*A61B 5/05* (2006.01)
*A61B 5/00* (2006.01)
*A61B 5/02* (2006.01)
*A61B 10/02* (2006.01)
*A61B 6/00* (2006.01)

(52) U.S. Cl.
CPC .......... *A61B 5/0066* (2013.01); *A61B 5/0084* (2013.01); *A61B 5/02007* (2013.01); *A61B 10/0275* (2013.01); *A61B 6/504* (2013.01); *A61B 2010/0208* (2013.01)

(58) Field of Classification Search
USPC ....................................................... 600/425
See application file for complete search history.

(56) References Cited

U.S. PATENT DOCUMENTS

| 5,897,567 | A  | * | 4/1999  | Ressemann et al. | .......... | 606/159   |
| 7,083,589 | B2 | * | 8/2006  | Banko et al.     | .......... | 604/22    |
| 2002/0016564 | A1 | * | 2/2002  | Courtney et al.  | .......... | 604/96.01 |
| 2004/0234206 | A1 | * | 11/2004 | Hamm et al.      | .......... | 385/53    |

(Continued)

FOREIGN PATENT DOCUMENTS

| JP | 2001-79007 A   | 3/2001 |
| JP | 2001-258831 A  | 9/2001 |

(Continued)

OTHER PUBLICATIONS

International Search Report (PCT/ISA/210) dated Jan. 25, 2011, by the Japanese Patent Office as the International Searching Authority for International Application No. PCT/JP2010/007593.

*Primary Examiner* — Amelie R Gillman
(74) *Attorney, Agent, or Firm* — Buchanan Ingersoll & Rooney PC (57) ABSTRACT

A probe including a catheter sheath, a shaft inserted inside the catheter sheath, and an attachment portion detachably attached to a rotational drive unit, wherein the attachment portion includes an isolation member isolating the inside of the attachment portion into a first area in which a member for transmitting the drive force generated by the rotational drive unit to the shaft is rotatably held and a second area in which the catheter sheath is fixedly held; the isolation member includes: an insertion hole through which the shaft is inserted between the first area and the second area and an ejection hole provided in a surface to which an end portion on the rotational drive unit side of the catheter sheath is connected and which is approximately perpendicular to the rotation axis of the shaft; and the ejection hole defines a flow path extending to the outside of the isolation member.

19 Claims, 9 Drawing Sheets

(56) References Cited

U.S. PATENT DOCUMENTS

2007/0244391 A1* 10/2007 Hirota .......................... 600/443
2008/0319341 A1* 12/2008 Taylor ................ A61B 10/0275
                                                           600/567

FOREIGN PATENT DOCUMENTS

| JP | 2003-339619 A | 12/2003 |
| JP | 2007-235055 A | 9/2007 |
| JP | 2009-240711 A | 10/2009 |

\* cited by examiner

PROBE AND OPTICAL IMAGING APPARATUS FOR DIAGNOSIS

CROSS REFERENCE TO RELATED APPLICATION

This application is a continuation of International Application No. PCT/JP2010/007593, filed on Dec. 28, 2012, which claims priority to Japanese Patent Application JP2010-064873 filed in Japan on Mar. 19, 2010, the entire contents of which are incorporated herein by reference.

FIELD OF THE INVENTION

Disclosed herein by way of exemplary embodiments are a probe and an optical imaging apparatus for diagnosis.

BACKGROUND DISCUSSION

An optical coherent tomography imaging apparatus for diagnosis (OCT) (for example, see Japanese unexamined patent publication No. 2001-79007) or an optical frequency domain imaging (OFDI) apparatus utilizing wavelength sweep, which is an improved type of OCT, are widely utilized for diagnosis before an operation through treatment inside a blood vessel with a high functional catheter such as a balloon catheter, a stent or the like, or for a result confirmation after an operation (hereinafter, in this disclosure, the optical coherent tomography imaging apparatus for diagnosis (OCT) and the optical frequency domain imaging (OFDI) apparatus utilizing wavelength sweep will be generically referred to as "optical imaging apparatus for diagnosis").

In the aforementioned optical imaging apparatus for diagnosis, an optical probe unit includes an imaging core equipped with an optical lens or optical mirror (transmitting and receiving unit) attached at the distal end of an optical fiber cable. The optical probe unit is inserted inside a blood vessel and, while rotating the imaging core, a measurement light is emanated from the transmitting and receiving unit at the distal end into the blood vessel and concurrently, a radial scan inside the blood vessel is carried out for light-receiving reflected light from the biological tissue. Then, after generating interference light by making the aforementioned light-received reflected-light and reference light interfere with each other, a cross-sectional image of the blood vessel is visualized based on the aforementioned interference light.

For the radial scan of the imaging core, the scan is carried out generally by using a rotational drive unit referred to as a scanner and pull-back unit and the optical probe unit is detachably attached to the aforementioned rotational drive unit.

When performing measurements, it is necessary to protect the scanner and pull-back unit from liquid such as blood or the like. That is, problems may occur in the rotation drive when a liquid such as blood or the like gets into the scanner and pull-back unit at the time of measurement. Also, in a case in which the inside of the scanner and pull-back unit is contaminated, there is concern that intensity of the optical signal (measurement light or reflected light) may attenuate (optical loss may occur) and an erroneous diagnosis is induced caused by the fact that the image quality of the visualized cross-sectional image deteriorates.

SUMMARY

In the optical imaging apparatus for diagnosis in the past, it was possible to prevent the liquid such as blood or the like from intruding from the outside by covering the rotational drive unit, but it cannot be said that the protection was sufficient with respect to the intrusion from the inside. Specifically, in a situation in which a hole is formed at a portion of the catheter sheath caused by the sheath being hooked to the stent, a kink occurring, or an unreasonable load is applied when inserting the optical probe unit inside the blood vessel, for instance, there occurs a situation in which liquid will intrude inside the rotational drive unit due to the liquid such as blood or the like flowing backward along the inside of the catheter sheath.

In view of the above-mentioned problem, the disclosure herein provides a mechanism in which it is possible to prevent intrusion of the liquid into the rotational drive unit, even in a case where the liquid has flowed backward inside the catheter sheath in the probe attached detachably to the rotational drive unit of the optical imaging apparatus for diagnosis.

In order to achieve the above-mentioned object, according to an exemplary aspect, there is provided a probe which includes a catheter sheath, a shaft inserted inside the catheter sheath and transmitting a drive force for rotating a transmitting and receiving unit which carries out transmission and reception of light, and an attachment portion detachably attached to a rotational drive unit which generates the drive force transmitted by the shaft, wherein the attachment portion includes an isolation member for isolating the inside of the attachment portion into a first area in which a member for transmitting the drive force generated by the rotational drive unit to the shaft is rotatably held and a second area in which the catheter sheath is held in a fixed manner. The isolation member includes an insertion hole through which the shaft is inserted between the first area and the second area and an ejection hole provided in a surface to which an end portion on the rotational drive unit side of the catheter sheath is connected and which is approximately perpendicular to the rotation axis of the shaft, and the ejection hole constitutes a flow path which extends to the outside of the isolation member.

According to an exemplary aspect, it becomes possible, in the probe detachably attached to the rotational drive unit of the optical imaging apparatus for diagnosis, to prevent intrusion of the liquid into the rotational drive unit even in a case in which the liquid has flowed backward inside the catheter sheath.

DETAILED DESCRIPTION

Figure 1:
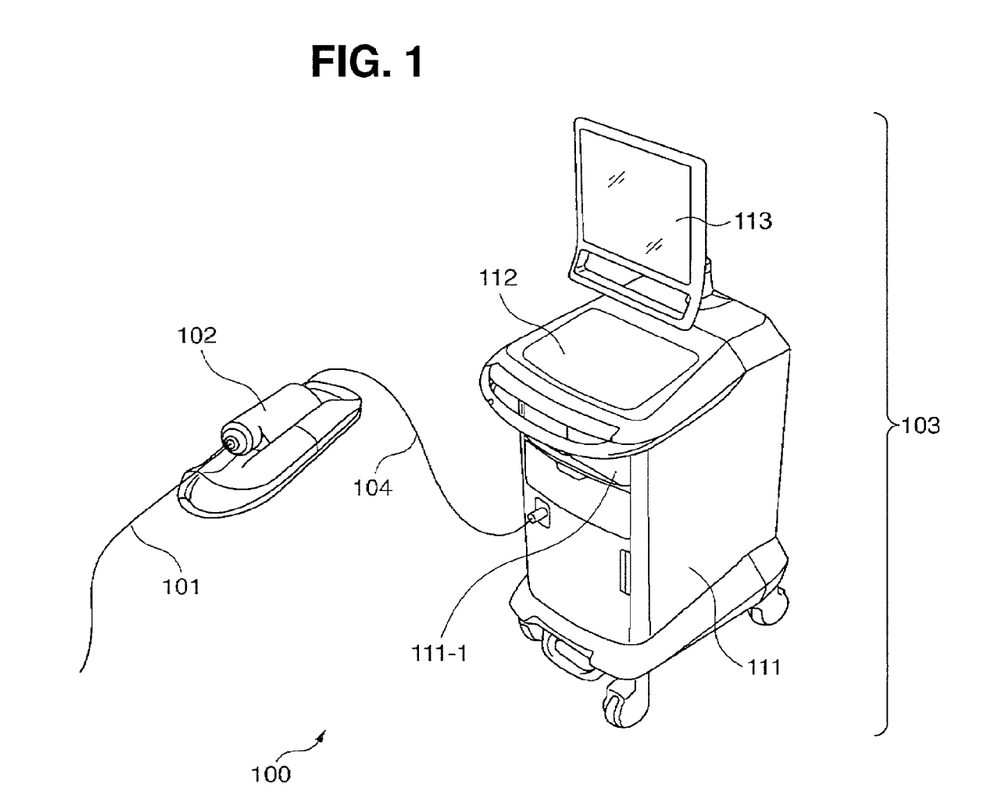
FIG. 1 is a schematic view showing an optical imaging apparatus for diagnosis according to an exemplified embodiment of the disclosure.

FIG. 1 is a schematic view showing an optical imaging apparatus for diagnosis (optical coherent tomography imaging apparatus for diagnosis or optical frequency domain imaging apparatus utilizing wavelength sweep) 100 according to a first exemplified embodiment of the disclosure.

As shown in FIG. 1, the optical imaging apparatus for diagnosis 100 is provided with an optical probe unit 101, a scanner and pull-back unit 102, also referred to as a rotational drive unit as mentioned above, and an operation control apparatus 103, and the scanner and pull-back unit 102 and the operation control apparatus 103 are connected by means of a signal line 104.

The optical probe unit 101 is inserted directly inside a body-cavity such as a blood vessel or the like and an imaging core is inserted therethrough which continuously transmits transmitted measurement light to the inside of the body-cavity and which, concurrently, is provided with a transmitting and receiving unit for continuously receiving reflected light from the inside of the body-cavity. In the optical imaging apparatus for diagnosis 100, the state inside the body-cavity is measured by using the imaging core.

The optical probe unit 101 is detachably attached to the scanner and pull-back unit 102 and the radial operation (operation in the axial direction and operation in the rotational direction inside the body-cavity) of the imaging core inserted inside the optical probe unit 101 is defined by driving a built-in motor. Also, there is obtained reflected light which is received in the transmitting and receiving unit and it is transmitted to the operation control apparatus 103.

For carrying out the measurement, the operation control apparatus 103 is provided with a function for inputting various kinds of set values and a function for processing data obtained by the measurement and for displaying them as blood vessel cross-section images.

In the operation control apparatus 103, the reference numeral 111 denotes a main body control unit, and it generates interference-light data by making the reflected light obtained by the measurement interfere with the reference light obtained by separating the measurement light and concurrently, a cross-section image is generated by processing line data generated based on the interference-light data. The reference numeral 111-1 denotes a printer and DVD recorder that prints process results in the main body control unit 111, stores them as data, and so on.

The reference numeral 112 denotes an operation panel and users may carry out inputting of various kinds of set values and instructions through the operation panel 112. The reference numeral 113 denotes an LCD monitor as a display apparatus and it displays the cross-section image generated in the main body control unit 111.

Figure 2:
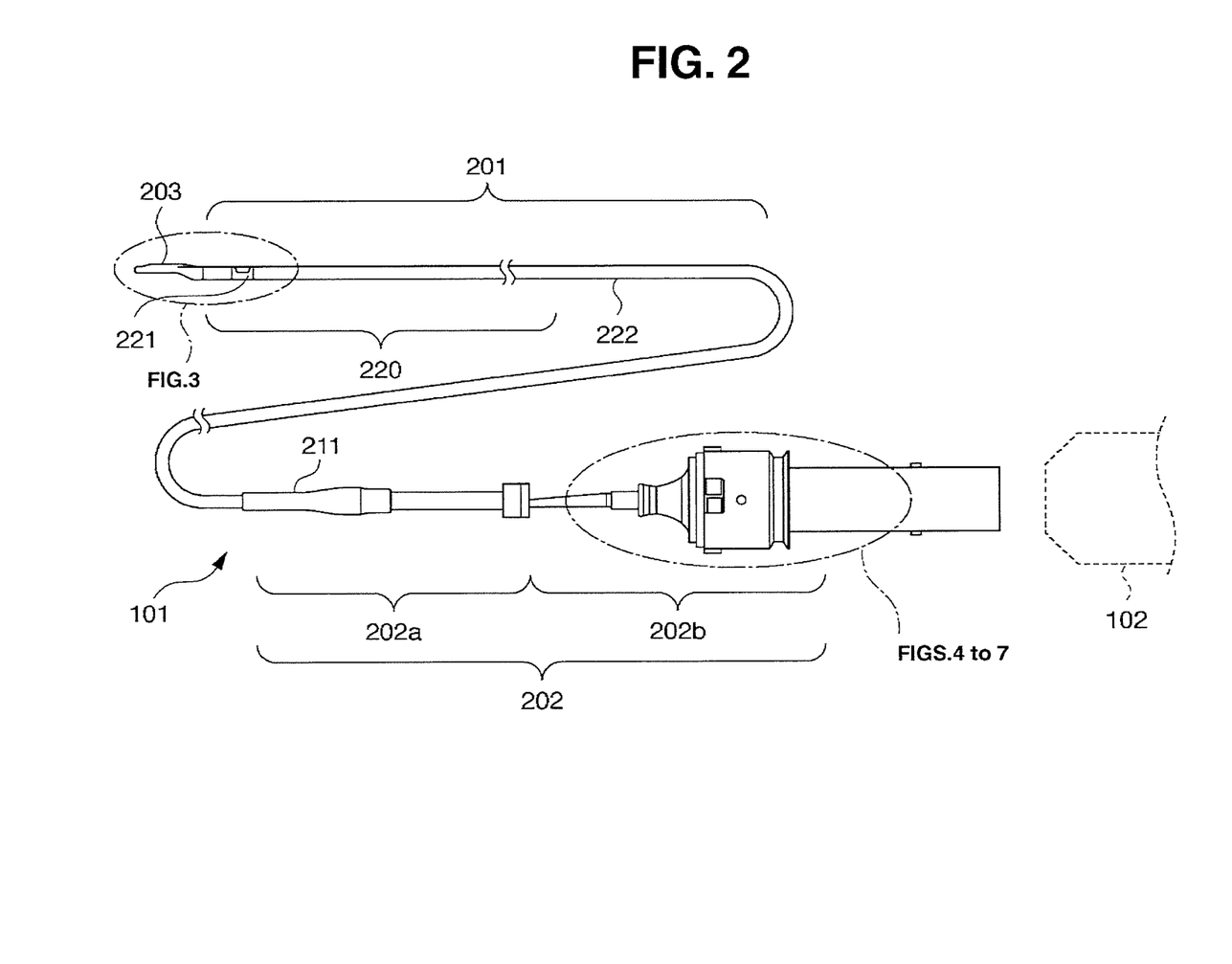
FIG. 2 is a schematic view showing an optical probe unit according to an exemplary aspect thereof.

With reference also to FIG. 2, the optical probe unit 101 includes a long-sized catheter sheath 201 configured to be inserted inside a blood vessel and a connector unit 202 arranged on the hand side of a user without being inserted inside the blood vessel in order to be operated by the user. At the distal end of the catheter sheath 201, a tube defines a guide wire lumen 203 (see FIG. 3 for details of the distal portion of the optical probe unit 101). The catheter sheath 201 forms a tubular lumen continuous from a connection portion with the tube for guide wire lumen 203 to a connection portion with the connector unit 202.

Inside the tubular lumen of the catheter sheath 201, over approximately the entire length of the catheter sheath 201, there is inserted therethrough an imaging core 220 provided with a transmitting and receiving unit 221 for transmitting and receiving measurement light and provided with a coil-shaped drive shaft 222 which incorporates an optical fiber cable in the inside thereof and which transmits rotational drive force for rotating the optical fiber cable.

The connector unit 202 includes a sheath connector 202a preferably integrated with the proximal end of the catheter sheath 201, and a drive shaft connector 202b which is fixed to the proximal end of the drive shaft 222 and enables the drive shaft 222 to rotate.

At the boundary portion between the sheath connector 202a and the catheter sheath 201, there is provided an anti-kink protector 211. Thus, a predetermined rigidity can be maintained and it is possible to prevent bending (kink) caused by a rapid change in material property.

The proximal end of the drive shaft connector 202b is detachably attached to the scanner and pull-back unit 102. In other words, it functions as an attachment portion. (See, FIGS. 4A to 7 for details of the proximal end of the drive shaft connector 202b).

Figure 3:
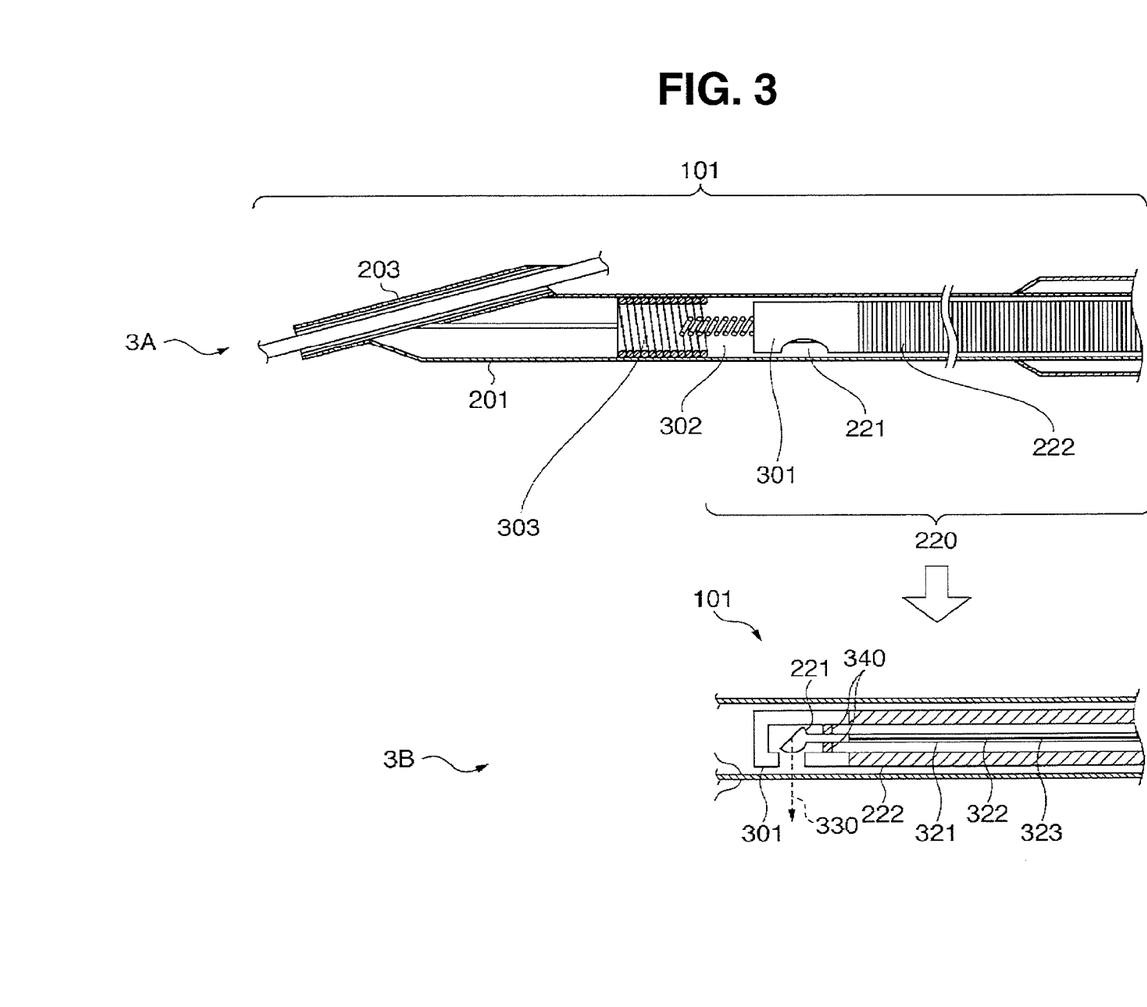
FIG. 3 is a schematic view showing the detailed configuration of a distal end of the optical probe unit shown in FIG. 2.

The distal portion of the optical probe unit 101 is shown by the reference numeral 3A in FIG. 3. Inside the intraluminal portion of the catheter sheath 201, approximately over the entire length, an imaging core 220 is inserted therethrough which is provided with a housing 301 where there is arranged a transmitting and receiving unit 221 for transmitting measurement light and for receiving reflected light. The imaging core 220 is also provided with a drive shaft 222 for transmitting rotational drive force for rotating the housing 301, such that the optical probe unit 101 is thereby formed.

In the transmitting and receiving unit 221, the measurement light is transmitted toward the tissue inside the body-cavity and concurrently, the reflected light from the tissue inside the body-cavity is received.

The drive shaft 222 is formed in a coil shape and an optical fiber cable (single mode optical fiber cable) 321 is arranged in the inside thereof.

The housing 301 is formed in a shape having a cut-away portion at a part of a short cylindrical metal pipe and it is formed by means of cutting of a metal cluster, MIM (Metal powder Injection Molding) or the like. The housing 301 includes the transmitting and receiving unit 221 in the inside thereof and the proximal side thereof is connected with the drive shaft 222. Also, a short coil shaped elastic member 302 is provided on the distal side thereof.

The elastic member 302 is a member obtained by forming a stainless steel wire into a coil shape. The elastic member 302 is arranged on the distal side of the housing 301 such that hooking the inside of the catheter sheath 201 is prevented when the imaging core 220 is moved forward and backward.

The reference numeral 303 denotes a reinforcement coil and it is provided in order to prevent sharp bending of a distal portion of the catheter sheath 201.

The tube defining the guide wire lumen 203 receives the guide wire inserted inside a body-cavity such as a blood vessel or the like beforehand and it is then used to introduce the catheter sheath 201 as far as a target lesion by the guide wire.

It is possible for the drive shaft 222 to make the transmitting and receiving unit 221 perform rotational movement and axial-direction movement with respect to the catheter sheath 201. The drive shaft 222 comprises, for example, a multiple and multi-layered closely-attached coil or the like composed of a metal wire of stainless steel or the like which is flexible and also has such a characteristic as can transmit rotation well.

As shown in FIG. 3, reference numeral 3B refers to the schematic showing of a cross-sectional view of the imaging core 202 disposed inside catheter sheath 201. Inside the housing 301, a sideways illumination type ball lens (transmitting and receiving unit) 221 is fixed by a marker 340 and an optical fiber cable 321 constituted by a clad portion 323 and core portion 322 is arranged inside the drive shaft. The measurement light transmitted from the transmitting and receiving unit 221 is thus illuminated to the biological tissue inside the body-cavity after passing through the catheter sheath inner surface and the catheter sheath outer surface (see arrow 330).

Figure 4A:
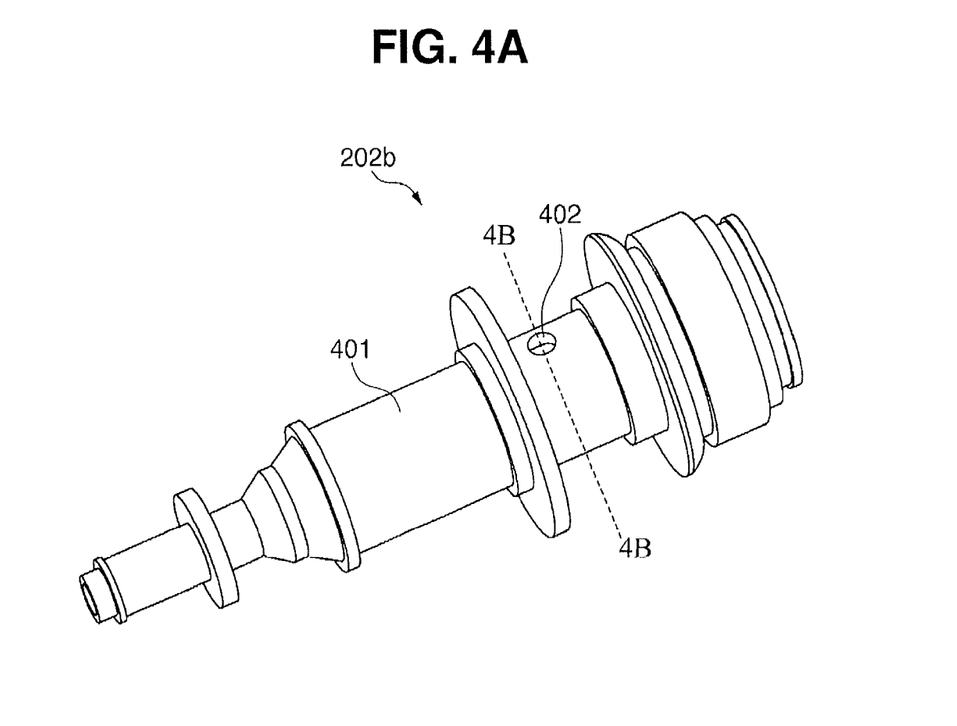
FIG. 4A is a schematic view showing a first outside housing at a proximal end of a drive shaft connector.

FIG. 4A illustrates a first outside housing 401 at the proximal end (scanner and pull-back unit 102 side) of the drive shaft connector 202b.

As shown in FIG. 4A, in the peripheral surface of the first outside housing 401, which forms a portion of the proximal end of the drive shaft connector 202b, a through-hole 402 is provided which passes though into the first outside housing 401. Thus, any liquid such as blood or the like which has flowed backward along the inside of the catheter sheath 201 is ejected via the through-hole 402 to the outside of the first outside housing 401.

Figure 4B:
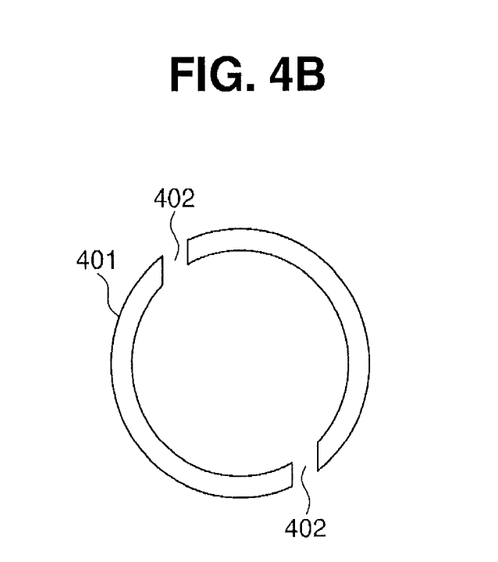
FIG. 4B is a cross section showing the first outside housing at the proximal end of the drive shaft connector, taken generally along line 4B-4B in FIG. 4A.

FIG. 4B is a cross-sectional view taken along line 4B-4B in FIG. 4A of the first outside housing 401 of the drive shaft connector 202b. As shown in FIG. 4B, the through-holes 402 are preferably arranged at positions opposing each other by 180 degrees in the peripheral surface of the first outside housing 401. Thus, whatever the direction along which the drive shaft connector 202b is disposed in the circumferential direction, the liquid such as blood or the like which has accumulated inside the drive shaft connector 202b can be ejected to the outside of the first outside housing 401.

Figure 5:
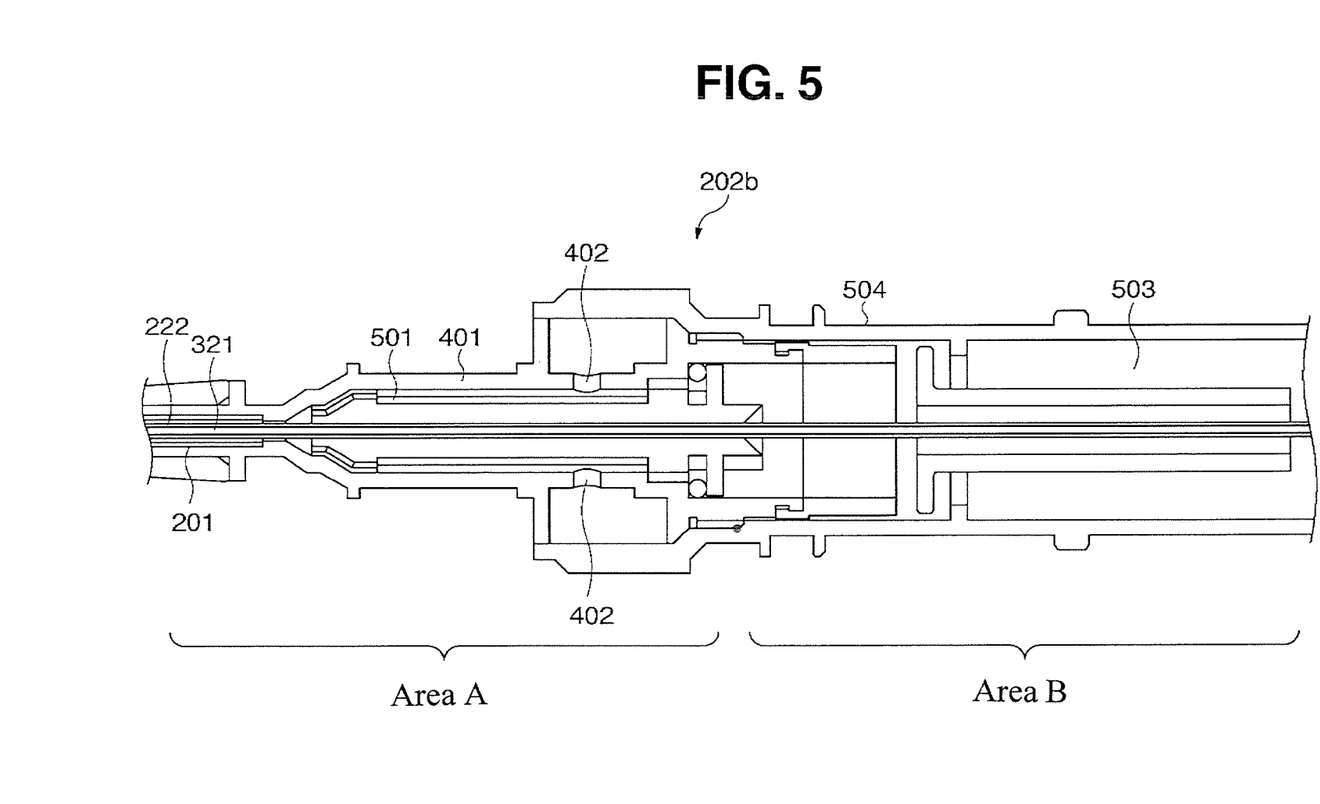
FIG. 5 is a cross-sectional view of a proximal end of a drive shaft connector.

FIG. 5 is a schematic illustration showing the cross section of the proximal end of the drive shaft connector 202b.

As shown in FIG. 5, the proximal end of the drive shaft connector 202b is provided with a first outside housing 401 and a second outside housing 504.

The first outside housing 401 is provided with a collar member 501 which defines the rotation axis of the drive shaft 222. The drive shaft 222 (including the optical fiber cable 321) inserted inside the catheter sheath 201 is connected to an optical connector 503 by passing through the aforementioned collar member 501.

The second outside housing 504 holds a portion of the first outside housing 401. The second outside housing also rotatably holds the optical connector 503 by which a rotation drive force generated in the scanner and pull-back unit 102 (rotational drive unit) is transmitted to the drive shaft 222.

In this manner, with respect to the drive shaft connector 202b of the optical probe unit 101 in this exemplified embodiment, the internal area covered by the first and second outside housings is isolated into two areas by the first outside housing and the collar member 501. That is, an area "A" in which each member is fixed and held on the first or second outside housing 401, 504 on the distal side from the collar member 501 and an area "B" in which each member is held on the second outside housing 504 in a rotatable manner on the proximal side from the collar member 501. In other words, in addition to the function which defines the rotation axis of the drive shaft 222, the collar member 501 functions as the isolation member which isolates or segregates the inside area of the drive shaft connector 202b.

Figure 6A:
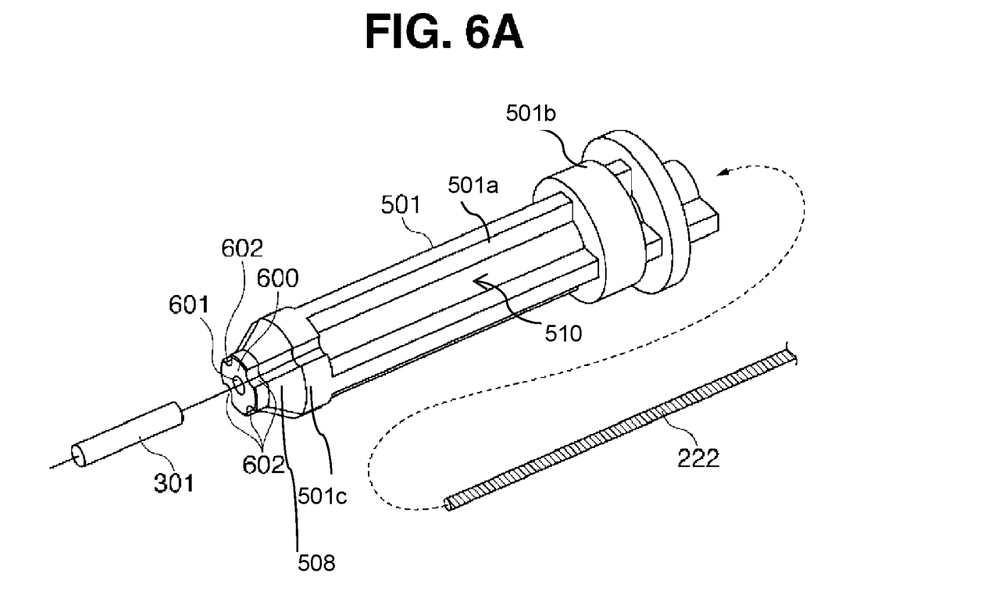
FIG. 6A is a schematic view showing a collar member and a protection member arranged at a proximal end of a drive shaft connector.

Referring also to FIG. 6A, the construction and functions of the collar member 501, which is arranged in the inside of the first outside housing 401 at the proximal end of the drive shaft connector 202b, will be explained.

As shown in FIG. 6A, the collar member 501 includes a distal end portion 501c, a proximal end portion 501b and a body portion 501a extending therebetween, a distalmost end 508 of the distal end portion 501c having a reduced diameter relative to the body portion 501a, and the body portion 501a having at least one groove 510 extending an entire axial length thereof. On the distal side of the collar member 501, an end surface 600 is provided which is approximately perpendicular with respect to the insertion direction toward which the drive shaft 222 is inserted. The end surface 600 includes an insertion hole 601, through which the drive shaft 222 is inserted, at a central position thereof and includes an ejection hole 602 for ejecting the liquid, such as blood or the like, which has flowed backward inside the catheter sheath 201 to the outside, at the peripheral portion thereof. In other words, the end surface 600 forms the terminal end (proximal side end) of the inside area of the catheter sheath 201.

Figure 6B:
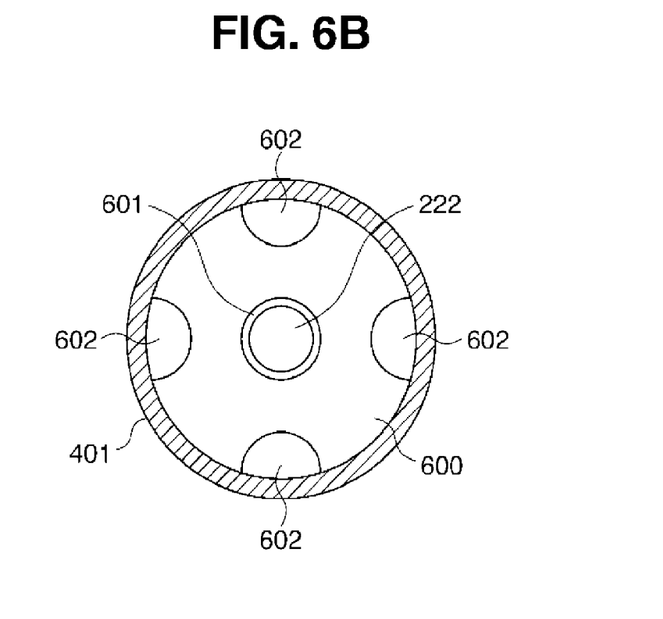
FIG. 6B is a cross-sectional view of the collar member and the protection member arranged at the proximal end of the drive shaft connector.

FIG. 6B is a plan view of the end surface 600. As shown in FIG. 6B, the inner diameter of the insertion hole 601 which is arranged at the central position of the end surface 600 is nearly equal to the outer diameter of the drive shaft 222, so that when the drive shaft 222 is inserted therein, only a relatively small gap is formed at the insertion hole 601.

On the other hand, the ejection hole 602, which is defined by a plurality of openings at the peripheral portion of the end surface 600, has a large diameter of a predetermined value when compared with the gap of the insertion hole 601. Consequently, the liquid such as blood or the like having a predetermined pressure, which has flowed backward inside the catheter sheath 201, goes toward the ejection hole 602 having the larger diameter when it is dammed up or obstructed at the end surface 600 which is the termination end.

In this manner, by employing a configuration in which ejection hole 602 has a cross-sectional area of a predetermined value which is equal to or greater than the cross-sectional area of the gap of the insertion hole 601, it becomes possible to direct the liquid such as blood or the like which has flowed backward inside the catheter sheath 201 under a predetermined pressure toward the ejection hole 602 side without it being directed toward the insertion hole 601 side. As a result, it becomes possible to repress or inhibit the amount of the liquid such as blood or the like which flows into the optical connector 503 side through the insertion hole 601 and it becomes possible to prevent its intrusion into the scanner and pull-back unit 102.

Figure 7:
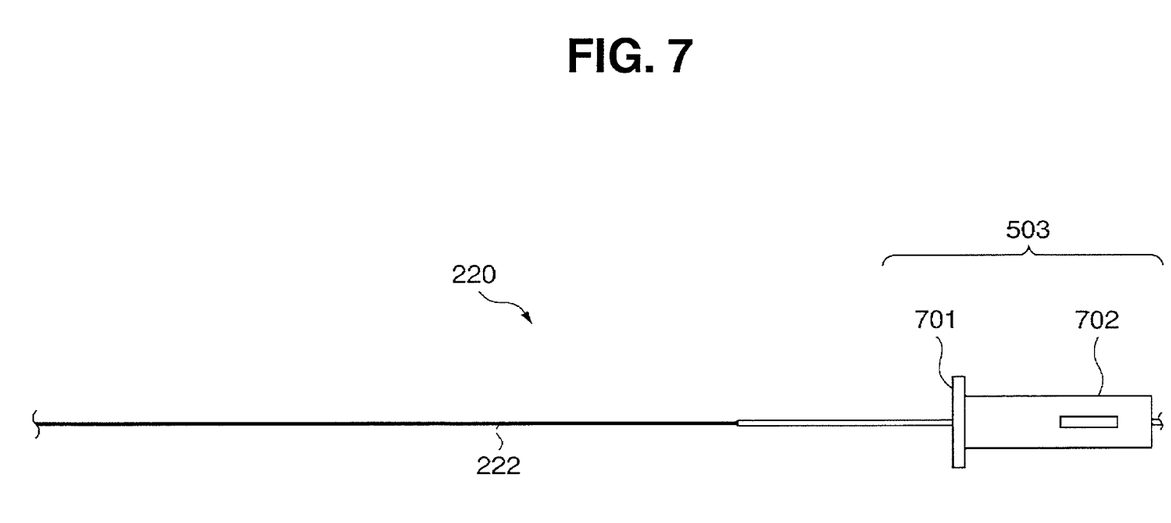
FIG. 7 is a schematic view showing an imaging core.

FIG. 7 illustrates the construction of the imaging core 220. As shown in FIG. 7, on the proximal side of the imaging core 220, the optical connector 503 is provided for optically connecting with an optical adapter inside the scanner and pull-back unit 102 when the drive shaft connector 202b is attached to the scanner and pull-back unit 102, and simultaneously, for transmitting the rotational drive force from the scanner and pull-back unit 102 to the drive shaft 222.

The optical connector 503 is provided with a connector fixing member 702 in which an APC optical connector (not shown) is arranged in the inside thereof and a flange 701 for fixing the connector fixing member 702 freely rotatably in the inside on the proximal side of the drive shaft connector 202b.

It is understood that the drive shaft 222 is joined to the APC optical connector arranged inside the optical connector 503, although not shown.

Figure 8A:
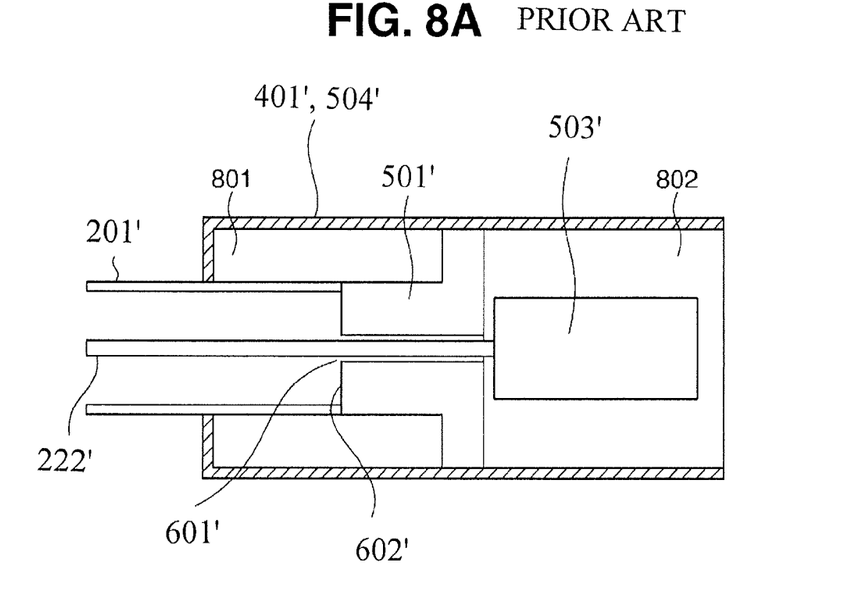
FIG. 8A is a schematic view explaining an ejection function at a proximal end of a drive shaft connector in a known device.

Next, the ejection function of the liquid such as blood or the like which has flowed backward inside the catheter sheath 201 at the proximal end of the drive shaft connector 202b will be explained. FIG. 8A is a schematic view at the proximal end of the drive shaft connector 202b as known in the prior art and FIG. 8B is a schematic view at the proximal end of the drive shaft connector 202b in the exemplified embodiment disclosed here.

As shown in FIG. 8A, with respect to the drive shaft connector 202b', the internal area thereof which is covered by the first and second outside housings 401', 504' is isolated into a first area 801 and a second area 802 by a collar member 501' or the like. The second area 802 is an area in which an optical connector 503' or the like is arranged and which is held rotatably with respect to the first and second outside housings. On the other hand, the first area 801 is an area in which the collar member 501' connected with the catheter sheath 201' side is fixed and held with respect to the first and second outside housings. Then, the drive shaft 222' lying inside of the second area 802 is inserted into the first area 801 through an insertion hole 601' of the collar member 501'.

Consequently, in the case of a known proximal structure of the drive shaft connector shown in FIG. 8A, the construction created a situation in which the liquid such as blood or the like which has flowed backward inside the catheter sheath is dammed up at the end surface of the collar member and flows toward the second area 802 along the insertion hole which forms the only flow path.

Figure 8B:
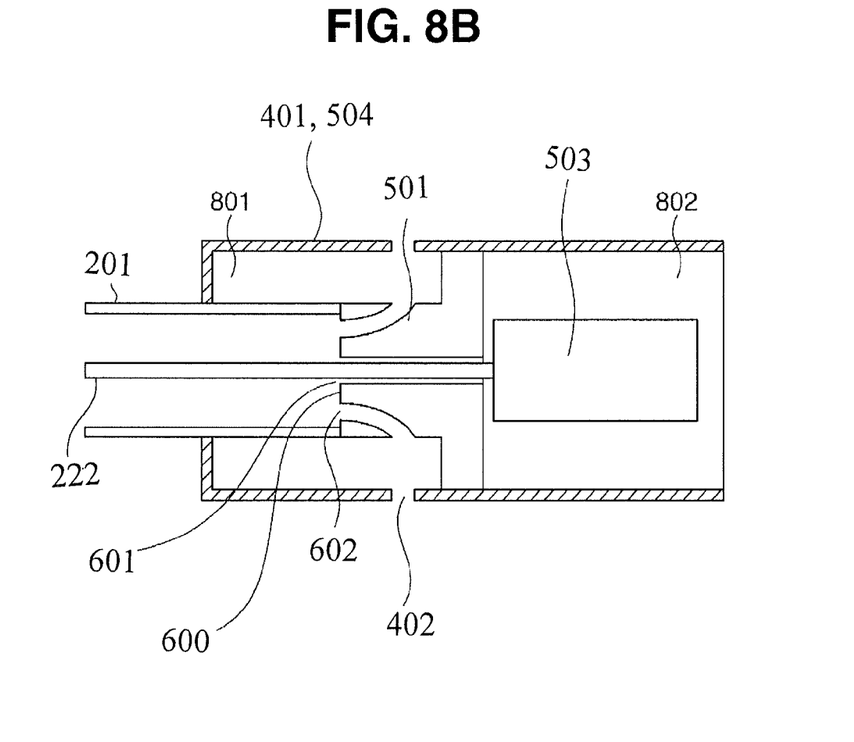
FIG. 8B is a schematic view explaining the ejection function at the proximal end of the drive shaft connector according to an exemplified embodiment of the disclosure.

On the other hand, as shown in FIG. 8B, in the case of employing a structure in which the ejection hole 602 is provided at the end surface 600 such as the proximal end of the drive shaft connector 202b as in this exemplified embodiment, it becomes a situation in which the liquid such as blood or the like which has flowed backward inside the catheter sheath 201 will flow into the first area 801 side along the ejection hole 602 having the lesser flow resistance when the liquid is dammed up at the end surface of the collar member 501 and thus, it is possible to prevent the liquid from flowing into the second area 802 along the insertion hole 601.

In the exemplary embodiment disclosed here, the liquid which flowed into the first area 801 is ejected to the outside through the through-holes 402 which are provided at the first and second outside housings 401, 504.

In this manner, by employing a construction in which the ejection hole is provided along the backward flow direction at the end surface perpendicular to the backward flow direction of the liquid such as blood or the like which has flowed backward inside the catheter sheath, it becomes possible to eject the aforementioned liquid reliably and it becomes possible to repress the amount of the liquid which flows into the second area along the insertion hole.

Figure 9:
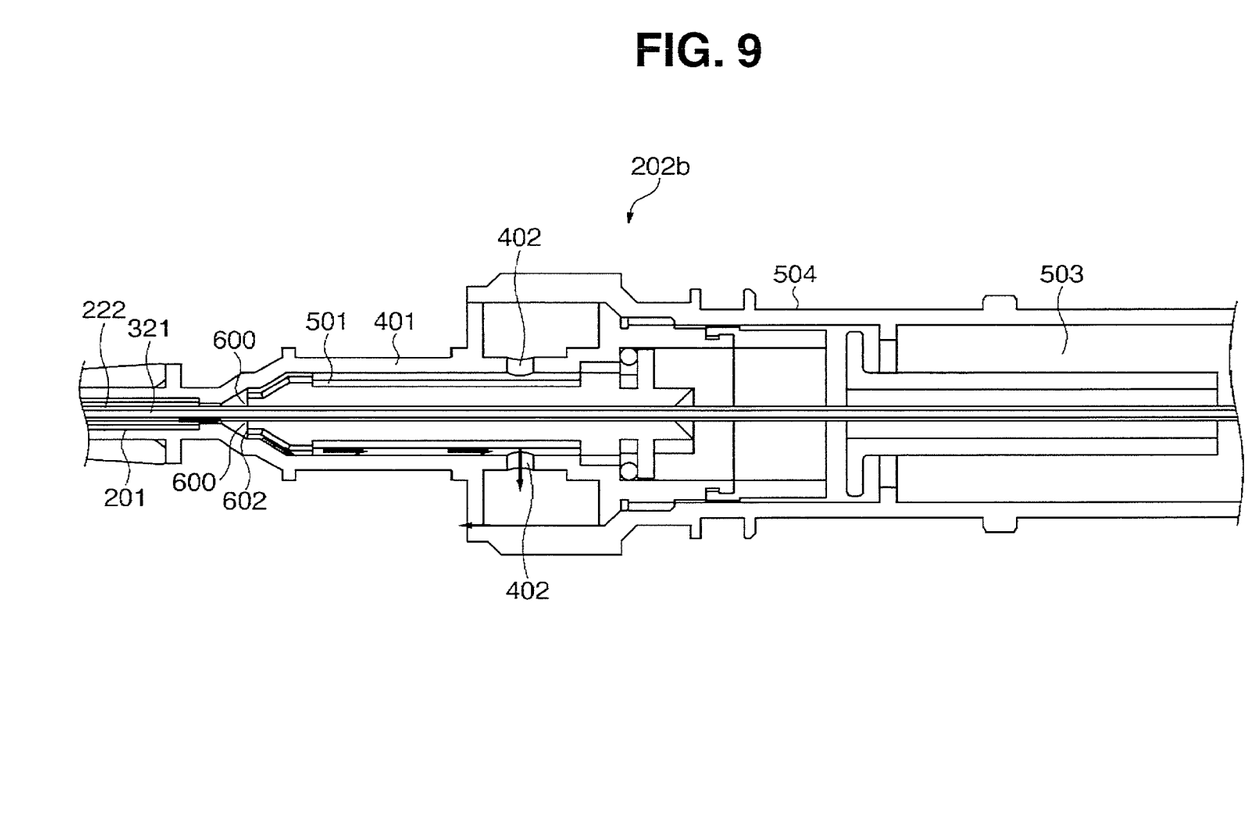
FIG. 9 is a schematic view showing an exemplary aspect in which a liquid such as blood having flowed backward inside a catheter sheath is ejected at a proximal end of a drive shaft connector.

FIG. 9 illustrates an aspect of the exemplified embodiment wherein the liquid such as blood or the like which has flowed backward inside the catheter sheath 201 is ejected at the proximal end of the drive shaft connector 202b.

The arrows shown in FIG. 9 indicate an ejection pathway of the aforementioned liquid. As shown in FIG. 9, when reaching the end surface 600, the liquid such as blood or the like which has flowed backward inside the catheter sheath 201, passes between the collar member 501 and the first outside housing 401 along the ejection hole 602 which is positioned on the lower side thereof, and is ejected from the first outside housing 401 at the through-hole 402 which is positioned on the lower side thereof. Further, the liquid ejected from the first outside housing 401 is ejected to the outside from the opening portion provided at the second outside housing 504 (or stored inside the second outside housing 504).

As is clear from the explanation above, for the optical probe unit in this exemplified embodiment, there is employed a construction at the proximal end of the drive shaft connector in which at the termination end of the inside area of the catheter sheath, at least one ejection hole is provided having a cross-sectional area larger than the gap of the insertion hole of the drive shaft.

Thus, there occurs a situation in which the liquid such as blood or the like which has flowed backward inside the catheter sheath is ejected from the ejection hole and it becomes possible to prevent the liquid from intruding into the scanner and pull-back side along the insertion hole.

In the above-mentioned first exemplified embodiment, there is employed a configuration in which four ejection holes are provided at the end surface 600 of the collar member 501, but the disclosure is not limited by this aspect and it is thus possible for the number of ejection holes to be more than four or less than four. However, regardless of the direction when placing the optical probe unit 101, it is desirable for there to be two or more holes at positions facing each other so as to be in an ejectable state.

Also, in the above-mentioned first exemplified embodiment, the cross section shapes of the ejection hole and the through-hole are shown as circular shapes, but the disclosure is not limited by this aspect and it is thus possible to employ other shapes.

Having described preferred exemplary embodiments of the disclosure with reference to the accompanying drawings, it is to be understood that the optical probe is not limited by those precise embodiments and that various changes and modifications could be effected therein by one skilled in the art without departing from the spirit or scope hereof, as defined in the appended claims.

What is claimed is:

1. A probe comprising:
a catheter sheath;
a drive shaft disposed inside the catheter sheath, the drive shaft configured for transmitting a drive force generated by a rotational drive unit; and
an attachment portion configured to be detachably attached to the rotational drive unit, the attachment portion including a first outside housing and a second outside housing, the first outside housing having a through hole;
wherein the attachment portion includes an isolation member for isolating the inside of the attachment portion into a first area in which a member for transmitting the drive force generated by the rotational drive unit to the drive shaft is configured to be rotatably held and a second area in which the catheter sheath is configured to be held in a fixed manner;
wherein the isolation member includes:
an end surface to which an end portion of the catheter sheath is connected, the end surface being approximately perpendicular to a rotation axis of the drive shaft;
a central insertion hole through which the drive shaft is configured to be inserted; and
an outer peripheral surface of the isolation member comprising at least one ejection groove, wherein, when the isolation member is disposed within the first outside housing, a combination of the at least one ejection groove and the first outside housing defines at least one ejection hole, the at least one ejection hole being separate and distinct from the insertion hole; and
an ejection flow path defined between the outer peripheral surface of the isolation member and an inner peripheral surface of the first outside housing such that a liquid entering the at least one ejection hole flows proximally along the ejection flow path and to the outside of the first outside housing via the through hole in the first outside housing;
wherein the insertion hole has a first diameter defining a first cross-sectional area and the drive shaft has a second diameter defining a second cross-sectional area, a difference between the first cross-sectional area and the second cross-sectional area defining a gap cross-sectional area, and
wherein a cross-sectional area of the at least one ejection hole is a predetermined value equal to or greater than the gap cross-sectional area such that the liquid entering the at least one ejection hole flows along the ejection flow path.

2. The probe according to claim 1, wherein the end surface includes the insertion hole arranged at a central position thereof and the at least one ejection hole arranged at a peripheral portion thereof.

3. The probe according to claim 1, wherein the ejection flow path further extends to outside of the attachment portion.

4. The probe according to claim 1, wherein the at least one ejection hole comprises a pair of ejection holes.

5. The probe according to claim 1, wherein the at least one ejection hole comprises four ejection holes.

6. The probe according to claim 2, wherein the isolation member defines a collar member, a terminal end surface of the collar member defining the surface including the insertion hole and the at least one ejection hole.

7. The probe according to claim 1, wherein the isolation member defines a collar member, wherein the collar member includes a distal end portion, a proximal end portion and a body portion extending therebetween, a distalmost end of the distal end portion having a reduced diameter relative to the body portion, and the body portion having at least one groove extending an entire axial length thereof.

8. The probe according to claim 7, wherein the at least one ejection groove formed in the outer peripheral surface of the isolation member is in fluid communication with the at least one groove of the body portion.

9. An optical imaging apparatus for diagnosis comprising:
a rotational drive unit; and
a probe according to claim 1 attached to the rotational drive unit,
wherein the probe further comprises an imaging core including a light transmitting and receiving unit; and
wherein the light transmitted and received by the light transmitting and receiving unit may be used to generate a cross-sectional image inside a body-cavity.

10. An optical imaging apparatus for diagnosis comprising:
an optical probe unit;
a rotational drive unit;
an operation control apparatus;
wherein the rotational drive unit and the operation control apparatus are connected by a signal line;
wherein the optical probe unit and the rotational drive unit are detachably connected;
wherein the optical probe unit comprises:
a catheter sheath configured to be inserted inside a blood vessel;
a connector unit; and
an imaging core disposed within the catheter sheath, the imaging core including a housing, a transmitting and receiving unit and a drive shaft disposed within the housing;
wherein the connector unit includes a sheath connector integrated with a proximal end of the catheter sheath and a drive shaft connector including a first outside housing including at least one through-hole and a second outside housing, a proximal end of the drive shaft connector being attached to the rotational drive unit;
wherein the drive shaft connector includes a collar member, an outer peripheral surface of the collar member comprising at least one ejection groove, wherein, when the collar member is disposed within the first outside housing, a combination of the at least one ejection groove and the first outside housing defines at least one ejection hole; and
an ejection flow path defined between an outer surface of the collar member and an inner surface of the first outside housing, whereby liquid which has flowed proximally along an inside of the catheter sheath is discharged to outside of the first housing via the ejection flow path and the at least one through hole; and
wherein the collar member includes a terminal end surface including an insertion hole through which the drive shaft is configured to be inserted, the insertion hole has a first diameter defining a first cross-sectional area and the drive shaft has a second diameter defining a second cross-sectional area, a difference between the first cross-sectional area and the second cross-sectional area defining a gap cross-sectional area, a cross-sectional area of the at least one ejection hole being equal to or greater than the gap cross-sectional area, whereby the at least one ejection hole provides lesser flow resistance than the insertion hole.

11. The optical imaging apparatus for diagnosis according to claim 10, wherein the collar member defines a rotation axis of the drive shaft.

12. The optical imaging apparatus for diagnosis according to claim 11, wherein the collar member defines an isolation member for isolating an inside of the proximal end of the drive shaft connector into a first area in which the transmitting and receiving unit and the drive shaft for transmitting the drive force generated by a rotational drive unit to the drive shaft is rotatably held, and a second area in which the catheter sheath is held in a fixed manner.

13. The optical imaging apparatus for diagnosis according to claim 11, wherein the transmitting and receiving unit is configured to transmit measured light and to receive reflected light such that a cross-sectional image of the blood vessel can be generated by the operation control apparatus.

14. The optical imaging apparatus for diagnosis according to claim 10, wherein the terminal end surface further includes the at least one ejection hole.

15. The optical imaging apparatus for diagnosis according to claim 14, wherein the insertion hole is disposed at a central position on the terminal end surface and the at least one ejection hole is disposed at a peripheral portion of the terminal end surface.

16. The optical imaging apparatus for diagnosis according to claim 14, wherein the at least one ejection hole comprises two ejection holes.

17. The optical imaging apparatus for diagnosis according to claim 14, wherein the at least one ejection hole comprises four ejection holes.

18. The optical imaging apparatus for diagnosis according to claim 10, wherein the collar member includes a distal end portion, a proximal end portion and a body portion extending therebetween, a distalmost end of the distal end portion having a reduced diameter relative to the body portion, and the body portion having at least one groove extending an entire axial length thereof.

19. The optical imaging apparatus for diagnosis according to claim 18, wherein the at least one ejection groove formed in the outer peripheral surface of the collar member is in fluid communication with the at least one groove of the body portion.

* * * * *